United States Patent [19]
McCue et al.

[11] Patent Number: 5,735,856
[45] Date of Patent: Apr. 7, 1998

[54] ORTHOPEDIC CUTTING GUIDE AND BUSHING

[75] Inventors: Diana F. McCue, Pocasset; Carl Livorsi, Lakeville; Paul Monteiro, Somerset, all of Mass.

[73] Assignee: Johnson & Johnson Professional, Inc., Raynham, Mass.

[21] Appl. No.: 792,037

[22] Filed: Jan. 31, 1997

[51] Int. Cl.⁶ .................................................. A61F 5/00
[52] U.S. Cl. ............................... 606/87; 606/88; 606/96
[58] Field of Search ............................. 606/88, 87, 96

[56] References Cited

U.S. PATENT DOCUMENTS

| | | | |
|---|---|---|---|
| 4,938,762 | 7/1990 | Wehrli | 606/88 |
| 5,053,037 | 10/1991 | Lackey | 606/79 |
| 5,100,409 | 3/1992 | Coates et al. | 606/88 |
| 5,176,684 | 1/1993 | Ferrante et al. | 606/86 |
| 5,387,216 | 2/1995 | Thornhill et al. | 606/88 |
| 5,415,662 | 5/1995 | Ferrante et al. | 606/86 |
| 5,514,140 | 5/1996 | Lackey | 606/80 |

FOREIGN PATENT DOCUMENTS

| | | | |
|---|---|---|---|
| 340176 | 3/1989 | European Pat. Off. | 606/88 |
| 466659 | 1/1992 | European Pat. Off. | 606/88 |

*Primary Examiner*—Michael Buiz
*Assistant Examiner*—Julian W. Woo
*Attorney, Agent, or Firm*—Nutter, McClennen & Fish, LLP

[57] ABSTRACT

An instrument for orthopedic surgery comprising a block or cutting guide having a recess, and at least one locking device located on the cutting guide. The locking device is selectively movable between a first position in which a portion of the locking device covers a portion of the recess and a second position in which the recess is unobstructed. A bushing having a portion adapted to removably and replaceably mate with the recess on the cutting guide is also disclosed. The instrument is particularly useful for distal femoral augmentation in knee revision surgery.

20 Claims, 4 Drawing Sheets

ORTHOPEDIC CUTTING GUIDE AND BUSHING

FIELD OF THE INVENTION

The invention relates to an instrument for use in orthopedic surgery, and more particularly, to an instrument used as a cutting guide for prosthetic joint revision surgery.

BACKGROUND OF THE INVENTION

Replacement of joints, such as knees and hips, with prostheses in human beings has become quite common. As replacements have become more common, the need to replace the artificial joints, known as revision surgery, has also become more common. Reasons for replacement include wear of the artificial joint, installation of a newer, stronger prosthesis or to address or readdress other issues relating to a patient's bone structure.

Removal of a previous prosthesis can cause destruction of a significant amount of bone tissue in the area where the prosthesis was attached. This renders it difficult to mount to the bone instruments that guide cutting tools used to resect the bone as required for installation of a new prosthesis. One approach for mounting instruments requires placement of an intramedullary alignment rod into the bone being resected. Then, instrumentation, such as drilling guides, cutting guides and the like, may be located on the intramedullary alignment rod.

U.S. Pat. No. 5,387,216 provides an example of intramedullary rod based instruments for total knee revision, wherein a notch guide is located on the rod by means of a handle. A dovetail joint connects the handle to the notch guide. However, instruments configured for use with dovetail joints can be heavy, difficult to position correctly and could impede access to the surface of the bone being resected. Furthermore, the instrument does not include structures for securely binding the notch guide to the rod to prevent movement of the instrument during surgery.

In another example, U.S. Pat. No. 5,053,037 discloses femoral instrumentation that is located on the femur by means of an elongated drill/reamer. A removable collet is used to locate a drilling guide with respect to the drill/reamer. The removable collet resides in an elongated slot in the drilling guide and is registered on posts which may be provided with spring loaded locking means, such as a spring loaded ball. Instruments located by collets that are held in place by spring balls can suffer from many of the problems described with regard to instruments that are held in place by dovetail joints. Further, spring balls may have a limited life.

Instruments such as those described above have helped to improve the accuracy of bone resection, and in particular, resection of the distal portion of a femur for the introduction of a prosthesis. However, devices capable of providing a more secure connection of an instrument to an intramedullary rod are needed to move to the next level of accuracy.

SUMMARY OF THE INVENTION

The present invention provides a medical instrument including a block, such as a cutting guide, and a bushing securable to the cutting guide. A locking device associated with the cutting guide securely binds the bushing to the cutting guide.

In an exemplary embodiment, a medical instrument for orthopedic surgery includes a block having a first face, a second face, a passage through the block from the first face to the second face, a first recess formed in the first face, and a second recess formed in the first face that is separated from the first recess. A locking device is secured to the first surface of the block, wherein a portion of the locking device is selectably positionable over a portion of the first recess. A bushing defining a bore, is receivable within the first recess to align the bore with at least a portion of the passage through the block. The bushing can include a first flange receivable within the first recess of the block, an intermediate portion defining the bore, and a second flange receivable within the second recess.

The bore through the bushing can be offset to one side of the bushing and the bore can also be offset from the longitudinal axis of the bushing. Furthermore, the bore through the bushing can be angled. A protuberance can be provided on one of the flanges of the bushing for insertion into a complimentary secondary recess defined in the recess that is dimensioned to receive the flange.

The block can include a bias element, such as a spring washer, that urges a face of the locking device, including a notch, toward the first face of the block. A notch engagement element, such as a sphere that is partially disposed within the block and which is rotatable with respect to the block, enters the notch when a selected portion of the locking device is positioned over a portion of the first recess and a portion of the bushing.

BRIEF DESCRIPTION OF THE DRAWINGS

The invention will be more fully understood from the following detailed description taken in conjunction with the accompanying drawings, in which.

DETAILED DESCRIPTION OF THE INVENTION

Figure 1:
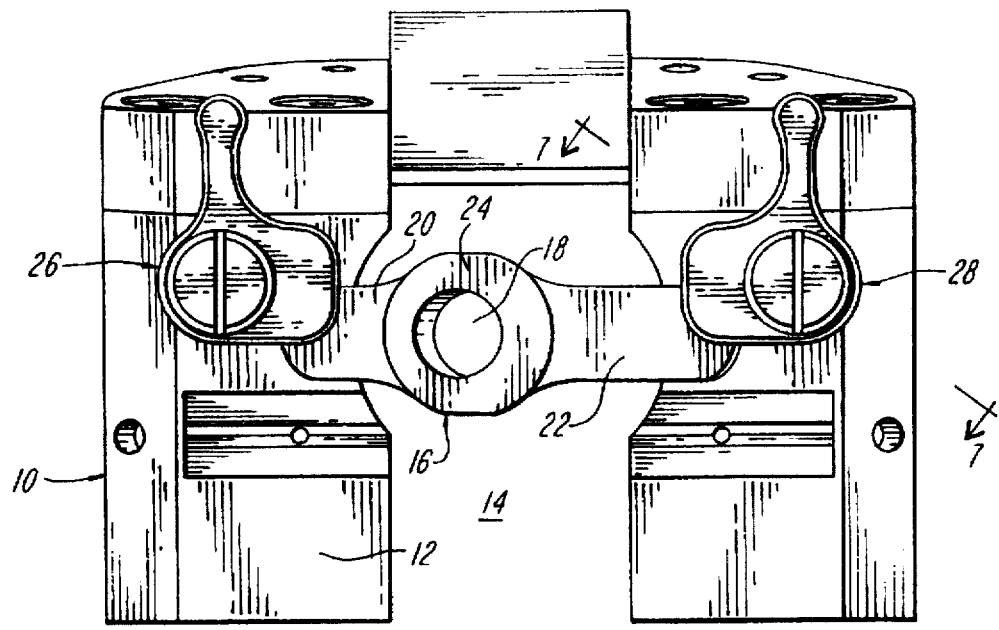
FIG. 1 is a view of a cutting guide and bushing in accordance with the present invention.

Referring now to FIG. 1, a medical instrument is illustrated that includes a block or cutting guide 10 having a first face 12 and a second face (not shown) opposite the first face. The cutting guide 10 defines a passage 14 through the cutting guide from the first face to the second face. A bushing 16 is shown mated to the cutting guide 10 so as to transect or cross at least a portion of the passage 14. The bushing defines a bore 18 that is aligned with at least a portion of the passage 14. Although the bushing can be variously configured, in FIG. 1 the bushing is shown as an elongate body that includes a first flange 20, a second flange 22, and an intermediate portion 24 between the first and second flanges. First and second locking devices 26 and 28, respectively, are secured to the first face 12 of the cutting guide 10 and are selectively positionable, as described in greater detail below, to trap a portion of the bushing 16 within the cutting guide 10.

Figure 2:
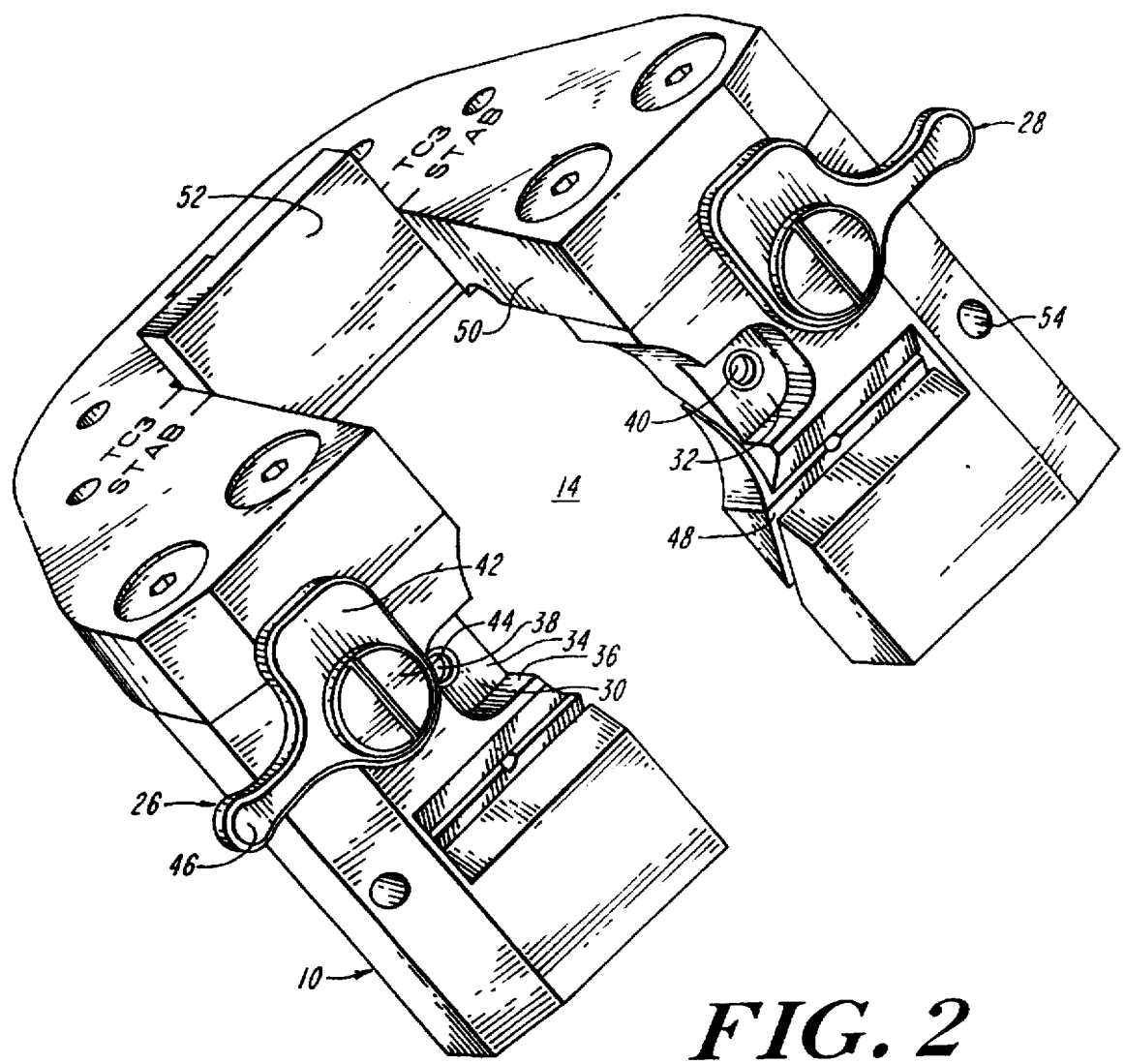
FIG. 2 is a perspective view of the cutting guide shown in FIG. 1 without a bushing.

Referring now to FIG. 2, the cutting guide 10 is shown without a bushing 16 in order to reveal features of the cutting guide obscured by the bushing in FIG. 1. In the illustrated embodiment, the cutting guide 10 includes a first recess 30 separated from a second recess 32 in opposition across the passage 14. Fewer or additional recesses can be provided as desired to correspond with the configuration of a selected bushing 16.

In an exemplary cutting guide 10, each recess abuts and opens into the passage 14. Each recess further includes a surface 34 which is substantially parallel to the first face 12, and a side wall 36. The exemplary recesses 30 and 32 are substantially rectangular in shape with rounded corners and are substantially identical. While the rectangular shape may be advantageous, any recess configuration which comports with the objects of the invention may be used. Such configurations could include, for example, an annular recess with a circumferential side wall.

The recesses 30 and 32 can be provided with secondary recesses 38 and 40, respectively. As shown the secondary recesses 38 and 40 are substantially cylindrical and are generally located in a central portion of a wall portion that defines the distal end of the recesses 30 and 32.

In the exemplary embodiment shown in FIG. 2, the first locking device 26 is associated with the first recess 30 and the second locking device 28 is associated with the second recess 32 in such a way as to allow at least portions of each locking device to be selectively positionable over at least a portion of each respective recess in the cutting guide 10. Each of the exemplary locking devices 26, 28 includes a cover portion 42 rotatable about a screw 44 that is partially embedded within the cutting block 10. A handle portion 46 can be provided for leverage to rotate the cover portion 42.

Each locking device 26, 28 can be configured and positioned so that no portion of the locking device covers its respective recess 30, 32, thereby defining an unlocked position. Conversely, each locking device 26, 28 can be also be configured and positioned to cause some portion of the locking device to cover its respective recess 30, 32, thereby defining a locked position.

Figure 3:
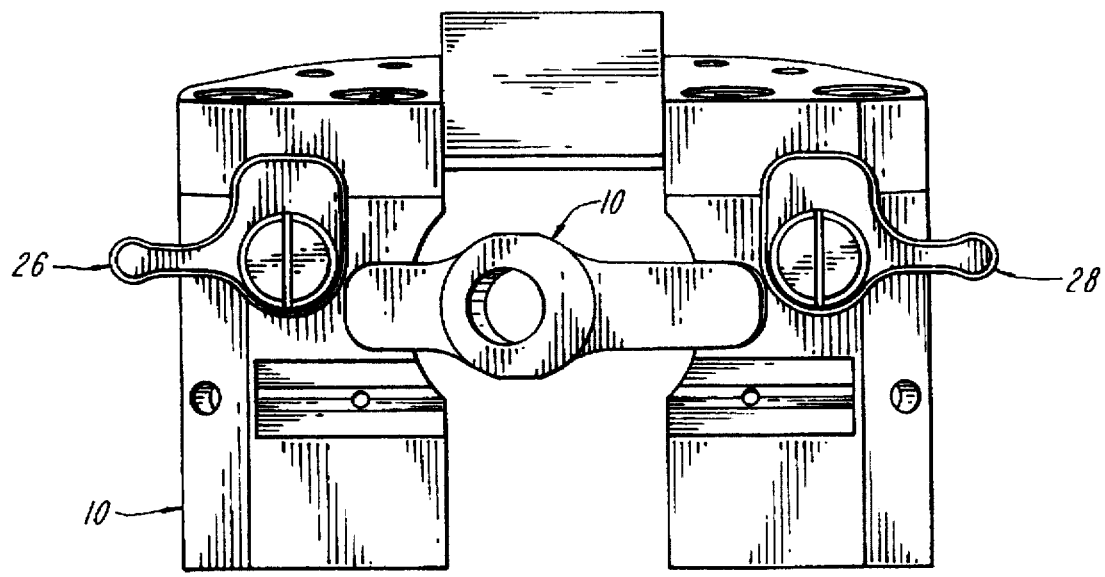
FIG. 3 is a view of the cutting guide and bushing shown in FIG. 1.

The operation of the exemplary selectively positionable locking devices 26 and 28 is further explained by reference to FIGS. 2, 3 and 1 in succession. In FIG. 2, the cutting guide 10 is shown without a bushing. The locking devices 26 and 28 are in the unlocked position. Now referring to FIG. 3, the bushing 16 has been mated to the cutting guide 10, but the locking devices 26 and 28 remain in the unlocked position as described above. Finally, referring to FIG. 1, the bushing 16 is shown mated to the cutting guide 10, and the locking devices 26 and 28 have been selectively moved to the locked position. Thus, the bushing 16 is tightly bound and substantially immovable with respect to the cutting guide 10.

Referring again to FIG. 2, the cutting guide 10 may also include one or more guide surfaces such as chamfer guides 48, notch guide surfaces 50, and a transverse cut guide surface 52. The depicted guide surfaces may be used by a surgeon to direct a saw or an osteotome to remove portions of bone as required. The cutting guide 10 may also be provided with a one or more holes 54 to allow for the insertion of pins (not shown), or more particularly, Steinman pins, during surgery to secure the cutting guide to a bone.

Figure 4:
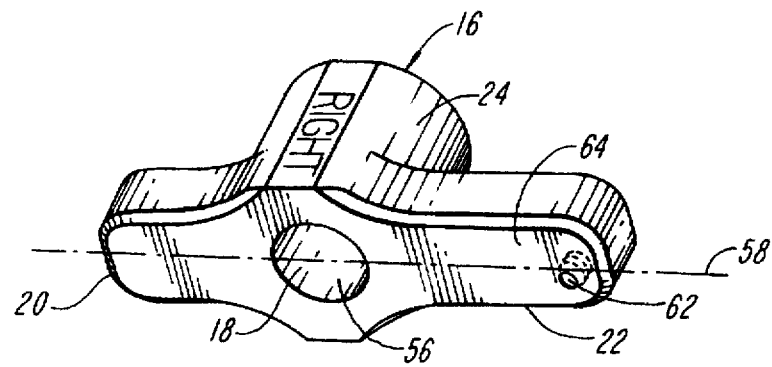
FIGS. 4–6 illustrate additional features and embodiments of the bushing shown in FIG. 1.
Figure 5:
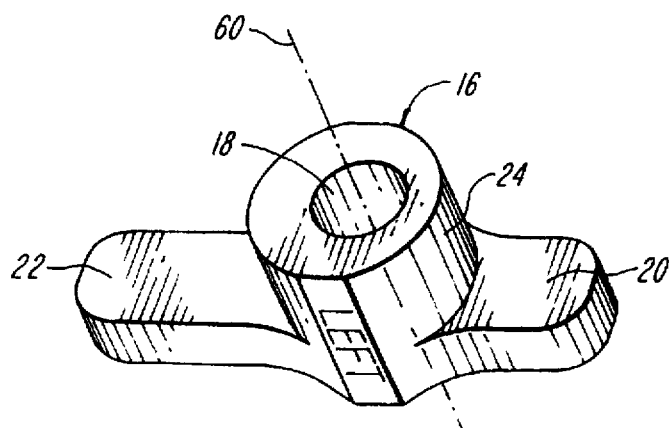
Figure 6:
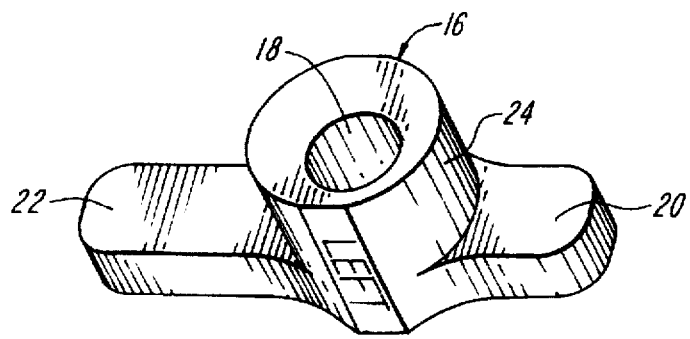

Additional features of the bushings are now described with respect to FIGS. 4–6, wherein the intermediate portion 24 of the bushing 16 is substantially cylindrical and thicker than the first flange 20 and the second flange 22. Regardless of whether the intermediate portion 24 of the bushing is thicker than the flanges 18, 22, and regardless of its shape, the intermediate portion, and more particularly the bore 18 can be offset longitudinally from a longitudinal center point 56 of the bushing as illustrated in FIGS. 4–6. Additionally, the bore defined by the intermediate portion can be offset laterally from a longitudinal axis 58 of the bushing as shown in FIG. 6.

The bushing 16 can define a plane that is substantially parallel with first face 12 of the cutting guide 10 when the bushing is received within the cutting guide, and the bore 18 defined by the intermediate portion 24 can include a longitudinal axis 60 that intersects the plane defined by the bushing at an angle less than 90 degrees to provide an angled bore. FIGS. 4 and 5 depict different views of the same exemplary bushing 16 to illustrate an angled bore 18, wherein one end of the bore is visible in FIG. 4 and a second end of the bore is visible in FIG. 5. Angulation of the bore 18 can be defined with respect to the angular deviation of the longitudinal axis of the bore 60 with respect to a plane defined by the bushing. In selected embodiments, the bore is angled 5° to 7° from the vertical.

Yet another feature of the invention is illustrated in FIG. 4, wherein a protuberance 62 extends from a surface 64 of one of the flanges. The protuberance 62 is receivable within the secondary recesses 38, 40 of either the first or the second recess 30, 32, respectively, depending on the orientation of the bushing 16 as it is mated with the cutting guide 10.

Figure 7:
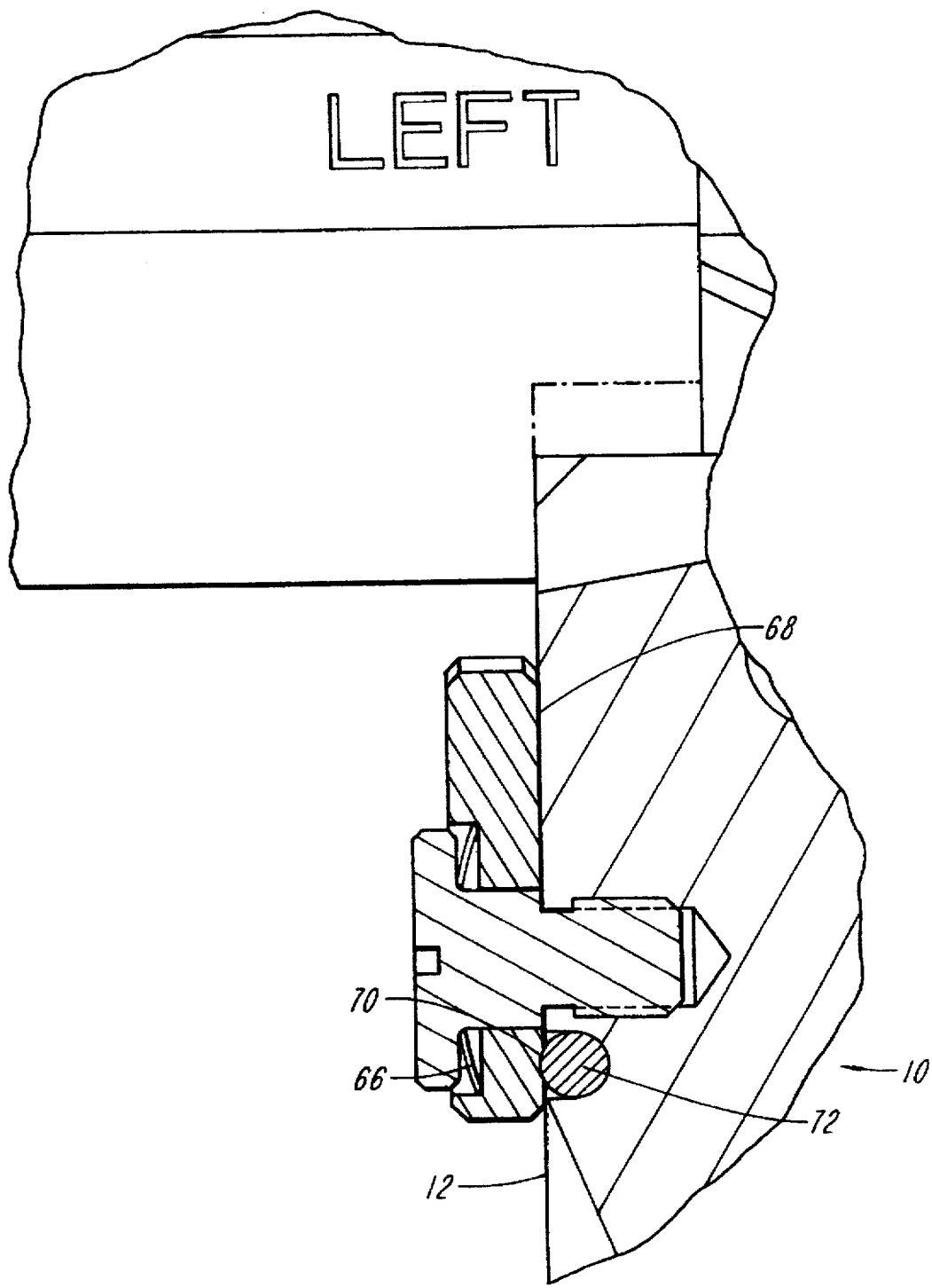
FIG. 7 is a partial sectional view of the cutting guide of FIG. 1 taken along line 7—7.

Additional features of an exemplary locking device are shown in FIG. 7, wherein the medical instrument further includes a bias element 66 such as a spring or curved washer that urges a face 68 of the locking device toward the first face 12 of the cutting guide. A notch 70 is defined in the face 68 of the locking device that is urged toward the first face 12 of the cutting guide. Extending from the first face 12 of the cutting guide is a notch engagement element 72 that enters the notch 70 when a selected portion of the locking device is positioned over a portion of the first recess and a portion of the bushing as shown and described above. In the illustrated embodiment, the notch engagement element 72 is a sphere that is partially disposed within the cutting guide and which is rotatable with respect to the cutting guide. Entry of a portion of the sphere 72 into the notch 70 can provide aural and/or tactile assurance that the locking device has reached the locked position. Depending upon the bias force provided by the bias element 66, the engaged sphere 72 and notch 70 can inhibit the locking device from becoming unintentionally unlocked.

The instrument described above may be used for knee revision femoral augmentation as follows. A bushing is selected and inserted into the cutting guide with the appropriate orientation, right or left, for the right or left femur. The bushing guide is next positively locked into place by rotating the locking devices into the locked position. The bore is mated with an intramedullary alignment rod and advanced to the distal surface of the femur. Steinman pins may be introduced through the cutting guide and into the femur as needed to prevent rotational movement of the guide about the intramedullary alignment rod and to hold the guide member in place for cuts that may be made after the intramedullary alignment rod is removed. Bilateral notch cuts and chamfers may then be made by directing an oscillating saw using guide surfaces provided in the cutting guide. The locking devices can be unlocked to remove the bushing and the intramedullary alignment rod from the femur without disturbing the position of the guide member. With the intramedullary alignment rod removed, transverse cuts may be made using a ½ inch blade or an osteotome. The proximal anterior chamfer may be fashioned in a like manner. It will be understood that the foregoing is only illustrative of the principles of the invention, and that various modifications can be made by those skilled in the art without departing from the scope and spirit of the invention.

What is claimed is:

1. A medical instrument for orthopedic surgery comprising:

a block having a first face, a second face, a passage through the block from the first face to the second face, and a first recess formed in the first face; and a locking device secured to the first face of the block, wherein a portion of the locking device is selectively positionable over a portion of the first recess.

2. The medical instrument of claim 1, further comprising a bushing defining a bore, at least a portion of the bushing being removably and replaceably mountable within the first recess.

3. The medical instrument of claim 2, wherein the bushing includes a body dimensioned to transect at least a portion of the passage through the block.

4. The medical instrument of claim 3, further comprising a second recess formed in the first face and separated from the first recess.

5. The medical instrument of claim 4, wherein the bushing includes a first flange receivable within the first recess of the block, an intermediate portion defining the bore, and a second flange receivable within the second recess.

6. The medical instrument of claim 5, wherein the intermediate portion of the bushing is substantially cylindrical and thicker than the first flange and the second flange.

7. The medical instrument of claim 5, wherein the bushing includes a longitudinal axis extending through the first flange, the intermediate portion and the second flange, and wherein the bore defined by the intermediate portion is offset longitudinally from a longitudinal center point of the bushing.

8. The medical instrument of claim 5, wherein the bushing includes a longitudinal axis extending through the first flange, the intermediate portion and the second flange, and wherein the bore defined by the intermediate portion is offset laterally from the longitudinal axis of the bushing.

9. The medical instrument of claim 5, wherein the bushing includes a longitudinal axis extending through the first flange, the intermediate portion and the second flange, wherein the bore defined by the intermediate portion is offset laterally from the longitudinal axis of the bushing and wherein the bore defined by the intermediate portion is offset longitudinally from a longitudinal center point of the bushing.

10. The medical instrument of claim 5, wherein the bushing defines a plane that is substantially parallel with first face of the block when the bushing is received within the block, and wherein the bore defined by the intermediate portion includes a longitudinal axis that intersects the plane defined by the bushing at an angle less than 90 degrees.

11. The medical instrument of claim 5, wherein the first recess and the second recess each include a secondary recess defined by the block, and wherein the first flange of the bushing includes a protuberance receivable within the secondary recess of one of the first recess and the second recess.

12. The medical instrument of claim 5, wherein the first flange and the second flange are on opposing sides of the intermediate portion and are substantially similar in shape.

13. The medical instrument of claim 5, wherein the first and the second recess each extend below the first face of the block a selected depth and wherein the first flange and the second flange have a thickness that is less than the selected depth.

14. The medical instrument of claim 13, wherein the intermediate portion has a thickness greater than the selected depth.

15. The medical instrument of claim 1, wherein the locking device is rotatably attached to the first face of the block.

16. The medical instrument of claim 15, wherein the locking device is rotatably attached to the first face by a screw.

17. A medical instrument for orthopedic surgery comprising:

a block having a first face, a second face, a passage through the block from the first face to the second face, a first recess formed in the first face, and a second recess formed in the first face that is separated from the first recess;

a locking device secured to the first face of the block, wherein a portion of the locking device is selectively positionable over a portion of the first recess; and a bushing defining a bore, at least a portion of the bushing being removably and replaceable and mountable within the first recess to align the bore with at least a portion of the passage through the block, the bushing including a first flange receivable within the first recess of the block, an intermediate portion defining the bore, and a second flange receivable within the second recess.

18. A medical instrument for orthopedic surgery comprising:

a block having a first face, a second face, a passage through the block from the first face to the second face, a first recess formed in the first face, and a second recess formed in the first face that is separated from the first recess, a first secondary recess defined by the block in a wall portion that defines the first recess, and a second secondary recess defined by the block in a wall portion that defines the second recess;

a bushing defining a bore, the bushing being removably and replaceably mountable within the first recess to align the bore with at least a portion of the passage through the block, the bushing including a first flange receivable within the first recess of the block, an intermediate portion defining the bore, a second flange receivable within the second recess, and a protuberance on the surface of the first flange that is receivable within one of the first and the second the secondary recess; and a locking device secured to the first face of the block, wherein a portion of the locking device is selectively positionable over a portion of the first recess and a portion of the bushing to inhibit removal of the bushing from the block.

19. The medical instrument of claim 18, wherein the block further includes a bias element that urges a face of the locking device toward the first face of the block, a notch is defined in the face of the locking device that is urged toward the first face of the block, and wherein the first face of the block includes a notch engagement element that enters the notch when a selected portion of the locking device is positioned over a portion of the first recess and a portion of the bushing.

20. The medical instrument of claim 19, wherein the notch engagement element is a sphere that is partially disposed within the block and which is rotatable with respect to the block.

* * * * *